United States Patent
Köbel

(10) Patent No.: US 10,278,847 B2
(45) Date of Patent: May 7, 2019

(54) SYSTEMS AND METHODS FOR REMOVING AIR FROM MEDICAL DEVICES

(71) Applicant: MOKITA MEDICAL GmbH i.Gr., Hamburg OT (DE)

(72) Inventor: Tilo Köbel, Hamburg (DE)

(73) Assignee: MOKITA MEDICAL GmbH i.Gr., Hamburg (DE)

( * ) Notice: Subject to any disclaimer, the term of this patent is extended or adjusted under 35 U.S.C. 154(b) by 253 days.

(21) Appl. No.: 15/234,572

(22) Filed: Aug. 11, 2016

(65) Prior Publication Data

US 2017/0042712 A1    Feb. 16, 2017

Related U.S. Application Data

(60) Provisional application No. 62/203,624, filed on Aug. 11, 2015.

(51) Int. Cl.
  *A61F 2/95* (2013.01)
  *A61B 90/70* (2016.01)
  *A61M 5/36* (2006.01)

(52) U.S. Cl.
  CPC .............. *A61F 2/95* (2013.01); *A61B 90/70* (2016.02); *A61M 5/36* (2013.01)

(58) Field of Classification Search
  CPC .................................. A61F 2/95; A61B 90/70
  See application file for complete search history.

(56) References Cited

U.S. PATENT DOCUMENTS

| | | |
|---|---|---|
| 4,875,480 A | 10/1989 | Imbert |
| 5,350,359 A | 9/1994 | Shaffer et al. |
| 5,427,104 A | 6/1995 | Briend et al. |
| 5,800,375 A | 9/1998 | Sweezer et al. |
| 5,817,046 A | 10/1998 | Glickman |

(Continued)

FOREIGN PATENT DOCUMENTS

| | | |
|---|---|---|
| EP | 0493677 B1 | 3/1998 |
| EP | 1779818 A2 | 5/2007 |

(Continued)

OTHER PUBLICATIONS

Celek, Atac and Ozcan Ozeke, Management of Coronary Air Embolism During Coronary Stenting, Kardiologia Polska, 2010; 68, 6: 716-718, Gaziosmanpasa University, Tokat, Turkey, www.kardiologiapolska.pl.

(Continued)

*Primary Examiner* — Ashley L Fishback
(74) *Attorney, Agent, or Firm* — William A. English; Vista IP Law Group LLP

(57) ABSTRACT

Systems and methods are provided for removing air from a medical device, such as a stent-graft and/or its delivery device. In an exemplary embodiment, the stent-graft or its delivery system or both are exposed to perfluorocarbon, by immersing the stent-graft or flushing the delivery device to remove air from the stent-graft. Optionally, the stent-graft and/or delivery system may be flushed multiple times, e.g., with perfluorocarbon before or after flushing with carbon dioxide, saline, a bio-inert gas, and the like. Thereafter, the stent-graft may be introduced into a patient's body and deployed at a target location, such as the site of an abdominal aortic aneurysm.

24 Claims, 1 Drawing Sheet

(56) References Cited

U.S. PATENT DOCUMENTS

| | | |
|---|---|---|
| 5,865,789 A | 2/1999 | Hattler |
| 6,106,497 A | 8/2000 | Wang |
| 6,117,102 A | 9/2000 | Schwartz et al. |
| 6,152,141 A | 11/2000 | Stevens |
| 6,241,699 B1 | 6/2001 | Suresh et al. |
| 6,534,002 B1 | 3/2003 | Lin et al. |
| 6,821,263 B2 | 11/2004 | Lenker et al. |
| 6,823,879 B2 | 11/2004 | Fillipi |
| 7,503,904 B2 | 3/2009 | Choi |
| 7,875,067 B2 | 1/2011 | Von Oepen et al. |
| 7,955,370 B2 | 6/2011 | Gunderson |
| 8,025,691 B2 | 9/2011 | Carter et al. |
| 8,480,627 B2 | 7/2013 | Christiansen |
| 8,628,490 B2 | 1/2014 | Yacoubian et al. |
| 8,740,976 B2 | 6/2014 | Tran et al. |
| 8,828,072 B2 | 9/2014 | Hoffman et al. |
| 9,038,564 B2 | 5/2015 | Fiorini et al. |
| 9,131,926 B2 | 9/2015 | Crisostomo et al. |
| 9,333,077 B2 | 5/2016 | Peter |
| 2002/0087119 A1 | 7/2002 | Parodi |
| 2002/0138126 A1* | 9/2002 | Camrud ............... A61F 2/95 623/1.11 |
| 2004/0171937 A1 | 9/2004 | Adams |
| 2007/0181157 A1 | 8/2007 | Dadourian |
| 2009/0005852 A1 | 1/2009 | Gittings et al. |
| 2009/0018486 A1 | 1/2009 | Goren et al. |
| 2010/0318114 A1 | 12/2010 | Pranevicius et al. |
| 2013/0079858 A1 | 3/2013 | Helkowski et al. |
| 2014/0100645 A1 | 4/2014 | Mayle et al. |
| 2014/0243873 A1 | 8/2014 | Franklin |
| 2014/0277403 A1 | 9/2014 | Peter |
| 2015/0209557 A1 | 7/2015 | Tal et al. |
| 2015/0297381 A1 | 10/2015 | Essinger et al. |
| 2015/0374401 A1 | 12/2015 | Guggenheimer et al. |

FOREIGN PATENT DOCUMENTS

| | | | |
|---|---|---|---|
| JP | WO 9203205 A1 * | 3/1992 | ............. B08B 3/041 |
| WO | 9203205 A1 | 3/1992 | |
| WO | 02054990 A2 | 7/2002 | |
| WO | 03002020 A2 | 1/2003 | |
| WO | 2006089517 A1 | 8/2006 | |

OTHER PUBLICATIONS

Kölbel, Tilo, et al., Carbon Dioxide Flushing Technique to Prevent Cerebral Arterial Air Embolism and Stroke During TEVAR; Journal of Endovascular Therapy, 2016, 1-3, www.jevt.org.

European Patent Office, International Search Report for corresponding International application No. PCT/IB2016/001237, Form PCT/ISA/210, dated Nov. 9, 2016, 5 pages.

European Patent Office, Written Opinion for corresponding International application No. PCT/IB2016/001237, Form PCT/ISA/237, dated Nov. 9, 2016, 7 pages.

* cited by examiner

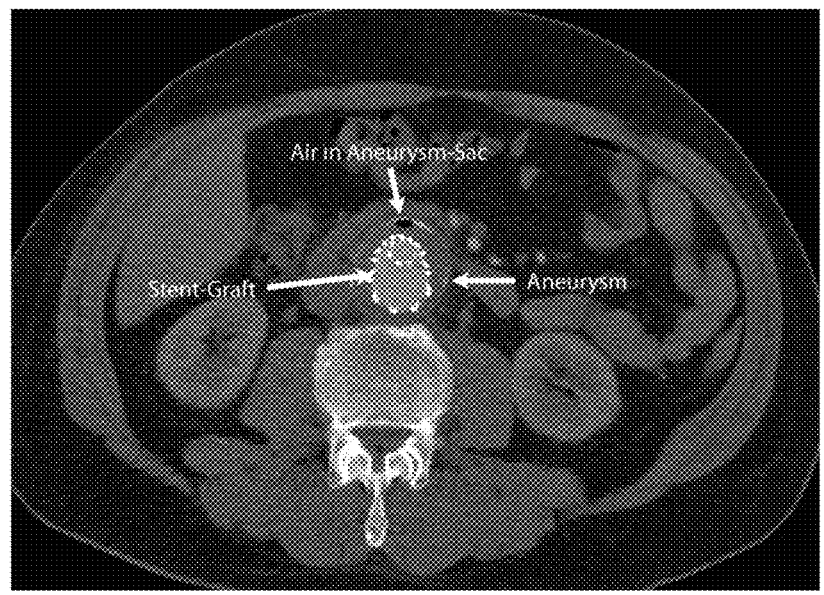
FIG. 1
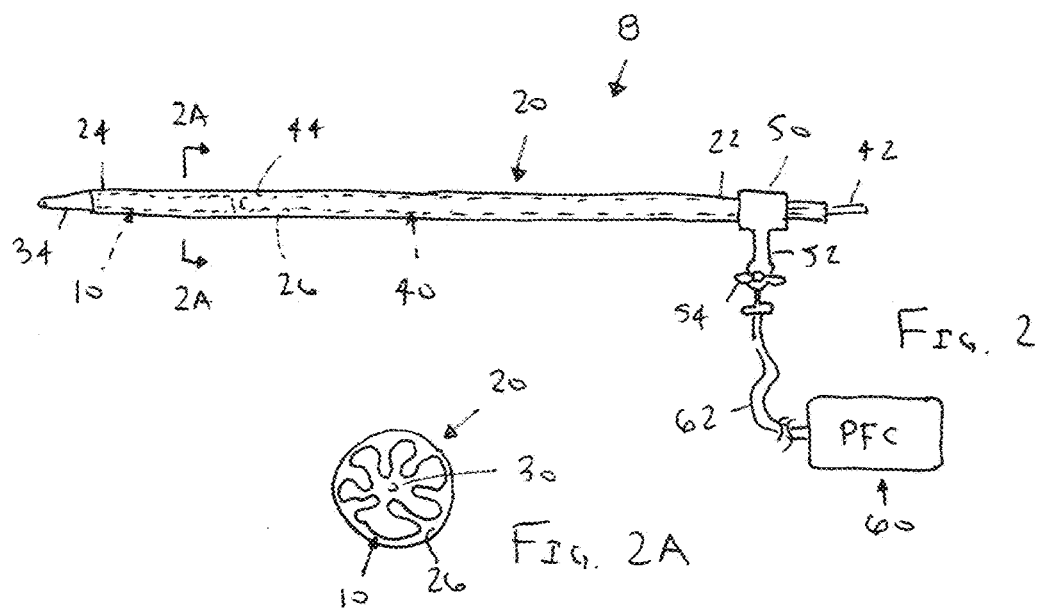

SYSTEMS AND METHODS FOR REMOVING AIR FROM MEDICAL DEVICES

RELATED APPLICATION DATA

The present application claims benefit of provisional application Ser. No. 62/203,624, filed Aug. 11, 2015, the entire disclosure of which is expressly incorporated by reference herein.

FIELD OF THE INVENTION

The present invention relates to devices, systems, and methods for removing gasses from medical devices, e.g., stent-grafts, stents, coils, and their delivery systems, e.g., before or after introduction into a patient's body, to reduce the risk of air embolism.

BACKGROUND

Endovascular aortic repair (EVAR) is a type of endovascular surgery used to treat pathology of the aorta. The most common EVAR treatment is of an abdominal aortic aneurysm, but many different types of aortic pathologies are treated by EVAR. When used to treat thoracic aortic disease, the procedure is then specifically termed TEVAR (thoracic endovascular aortic/aneurysm repair). The procedure involves placement of an expandable stent-graft within the aorta to treat the aortic disease without operating directly on the aorta. In 2003, EVAR surpassed open aortic surgery as the most common technique for repair of abdominal aortic aneurysm, and in 2010, EVAR accounted for 78% of all intact abdominal aortic aneurysm repair in the United States.

The procedure is carried out in a sterile environment under x-ray fluoroscopic guidance by a vascular surgeon, cardiac surgeon, interventional radiologist, general surgeon, or interventional cardiologist. The patient's femoral arteries are generally accessed percutaneously, e.g., with a surgical incision or direct puncture in the groin. Vascular sheaths are introduced into the patient's femoral arteries, through which one or more guide wires, catheters, and the stent-graft are introduced. The stent-graft acts as an artificial lumen for blood to flow through, thereby substantially isolating the aneurysm sac from direct blood flow and blood-pressure and thereby preventing further enlargement and rupture. The stent-graft is compressed into a catheter, introducer sheath, or other delivery system that allows the compressed stent-graft to be introduced from the femoral arteries to the intended place of deployment.

A stent-graft is typically an assembly of a fabric material and a metal frame or metal springs/stents and mounted on a catheter assembly. When introduced into the vasculature, stent-grafts are constrained to a smaller diameter to enable introduction by different techniques, such as a constraining sleeve or by loading into an introducer sheath. Stent-grafts, stents, and their catheter assemblies are typically produced, constrained, packed and, sterilized under room-air conditions. Consequently, spaces within a constraining sleeve or sheath that are not filled by the stent-graft or stent and/or the catheter assembly generally contain room air. For sterilization, the assemblies are packed in packaging, which is permeable for gas and are sterilized, e.g., using vacuum with ethyleneoxide-containing gas. The gas is removed by repeated vacuum and room air ventilation as a later step of the gas-sterilization process. Thus, when the product is delivered in its sterile packaging there is generally air present within the stent-graft assembly.

In the operating theatre, the stent-graft assemblies are unpacked from their packaging under sterile conditions. Air is removed from some stent-grafts and their catheter assemblies prior to introduction into the vasculature typically by flushing the sheath with isotonic solutions such as saline introduced through flushing ports that are part of the catheter assemblies. Stent-grafts that are constrained using a sleeve, such as the Gore TAG and cTAG device, are typically introduced into the vasculature without flushing to remove the room-air from the assembly.

It is well recognized that deployment of stent-grafts in the thoracic aorta involves a significant risk for stroke. It has been reported to be as high as 10% and is a major drawback of TEVAR.

While retrospective studies have been done, the pathomechanism of stroke as a complication of TEVAR is not well known. Generally, the main source for strokes are thought to be embolism by particles from thrombotic and atherosclerotic material adherent to the aortic wall, which is released by manipulation during deployment by wires, catheters, sheaths and the stent graft. Air-embolism by release of trapped air from the stent-graft during TEVAR may be a significant source of such strokes despite flushing techniques; however, it has been difficult to detect such events since the trapped air is not visible and they may only first recognized after the patient has woken up.

The risk of air-embolism and stroke during open surgery is well known and preventive strategies have been employed, e.g., in open cardiac surgery and neuro-surgery. Preventive strategies to avoid the introduction of air within endovascular devices into the human body include extensive saline flushing to mechanically squeeze out the air, which is present in catheters, stents (uncovered metal stents), coils, and other devices prior to introduction of these devices into the patient's vasculature. Such flushing with saline generally works well in these applications as air may be removed almost completely and so such flushing is generally part of the instructions for use of these devices.

With stent-grafts (prosthetic vascular grafts supported by metal stents), flushing with saline solution may not work well to remove air prior to introduction into the body. However, it is the method that is widely recommended and used today in most procedures. Because stent-grafts are combinations of stents with a fabric-covering, traditional mechanical flushing with saline may not work well because the fabric significantly hampers the ability to completely drive out the air. Also, factors like the degree of compression may influence the amount of "trapped air."

Another factor is the presence of side-branches and other advanced tools in modern stent-grafts and their delivery-systems, which may create pockets where air may be compressed during flushing, but not squeezed out. The trapped air may then be released during intravascular deployment of the procedure but may not be visually recognized during the procedure since air is not visible under fluoroscopy, which is generally used for such procedures. The released air may become visible on postoperative CT-scans after EVAR for abdominal aortic aneurysms in the aneurysm-sac days after the procedure, e.g., as shown in FIG. 1. Such occurrences are largely ignored because this air does not seem to cause much harm and is expected to be resorbed within weeks.

Trapped air may also be released when stent-grafts are deployed in segments of the aorta, which are close to brain-supplying arteries, the aortic trunk vessels, e.g., the innominate artery, left common carotid artery, and left subclavian artery. When such trapped air is released, there is a risk of air embolization into the brain. The same is true if these stent-grafts are released close to the coronary arteries, giving rise to a risk for air-embolization into the coronary arteries with a risk for myocardial infarction. Thus, insufficient removal of air from stent-grafts and/or their delivery systems before they are introduced into the vasculature may be a significant source of stroke during TEVAR.

Air is also known to be released from other medical devices used in neuroradiological procedures. For example, stents and coils and their delivery-assemblies, which are introduced in the arteries of the brain, may also contain air, which may potentially cause damage in the brain.

Accordingly, devices and methods that facilitate removing air or other gasses from medical devices, particularly stent-grafts, stents, coils and their delivery systems, to reduce the risk of embolism would be useful.

SUMMARY

The present invention is directed to devices and methods for removing gasses from medical devices, e.g., e.g., stent-grafts, stents, coils, and their delivery systems, before or after introduction into a patient's body, to reduce the risk of air embolism.

In accordance with one embodiment, a system is provided for flushing a medical device comprising an elongate delivery device comprising a proximal end, a distal end, a lumen extending between the proximal and distal ends, and a port on the proximal end communicating with the lumen, a prosthesis carried by the delivery device within the lumen, the system comprising a source of gas comprising one of carbon dioxide and a bio-inert gas connectable to the port for flushing the lumen with the gas to replace air within one or both of the prosthesis and the lumen with the gas; and a source of perfluorocarbon solution connectable to the port for flushing the lumen with the solution to absorb the gas from one or both of the prosthesis and the lumen into the solution.

In accordance with another embodiment, a method is provided for preparing a medical device that includes flushing the medical device with a gas to displace air from the medical device; and thereafter, flushing the medical device with perfluorocarbon to dissolve and remove the gas.

In accordance with still another embodiment, a system is provided for flushing air from a medical device that includes an elongate delivery device comprising a proximal end, a distal end, a lumen extending between the proximal and distal ends, and a port on the proximal end communicating with the lumen; a prosthesis carried by the delivery device within the lumen; and a source of perfluorocarbon solution connectable to the port for flushing the lumen with the solution to remove air from one or both of the prosthesis and the lumen.

In accordance with yet another embodiment, a method is provided for removing gas from a medical device that includes providing a source of perfluorocarbon; and exposing the medical device to perfluorocarbon from the source of perfluorocarbon to remove air from the medical device.

In accordance with still another embodiment, a method is provided for removing gas from a medical device that includes flushing the medical device with perfluorocarbon; and separately flushing the medical device with one or more of saline, carbon dioxide, and a bio-inert gas.

In accordance with another embodiment, a method is provided for removing air from one or both of a stent-graft and its delivery system that includes contacting the stent-graft or its delivery system or both with a perfluorocarbon for a time sufficient to remove a quantity air from the stent-graft, and thereafter introducing the stent-graft into a patient's body. A perfluorocarbon solution may, not just mechanically thrive out air within the stent-graft, but may absorb air present in the stent-graft and/or its delivery system, thereby reducing the risk of an air embolism when the stent-graft is introduced and deployed within a patient's body. For example, degassed perfluorocarbon may have a relatively high solubility for air such that may readily dissolve the air to remove it from exposure within the patient's body.

In accordance with another embodiment, a method is provided for removing air from one or both of a stent-graft and its delivery system that includes contacting the stent-graft or its delivery system or both with an emulsion comprising one or more perfluorocarbons for a time sufficient to remove a quantity of air from the stent-graft, and thereafter introducing the stent-graft into a patient's body.

In accordance with still another embodiment, a method is provided for removing air from one or both of a stent-graft and its delivery system that includes contacting the stent-graft or its delivery system or both with a degassed solution comprising perfluorocarbon or saline or both for a time sufficient to remove a quantity of air from the stent-graft, and thereafter introducing the stent-graft into a patient's body.

In accordance with yet another embodiment, a method is provided for removing air from one or both of a stent-graft and its delivery system that includes contacting the stent-graft or its delivery system or both with one or both of carbon dioxide and one or more bio-inert gases, such as helium or argon, with sufficient pressure and for a time sufficient to remove a quantity of air from the stent-graft, and thereafter flushing the stent-graft or its delivery system or both with another flushing solution, e.g., including saline or perfluorocarbon or a degassed solution containing perfluorocarbon or saline or both for a time sufficient to remove a quantity of carbon dioxide and one or more bio-inert gases, such as helium or argon, from the stent-graft, and thereafter introducing the stent-graft into a patient's body.

Other aspects and features of the present invention will become apparent from consideration of the following description taken in conjunction with the accompanying drawings.

BRIEF DESCRIPTION OF THE DRAWINGS

The drawings illustrate exemplary embodiments of the invention, in which:

FIG. 1 is an example of a postoperative CT-scan showing released air after implanting a stent-graft during an EVAR procedure.

FIG. 2 is a side view of an introducer sheath carrying a stent-graft showing an exemplary system for removing air from the stent-graft and introducer sheath using a source of perfluorocarbon.

FIG. 2A is a cross-section of the system of FIG. 2 taken across 2A-2A.

DETAILED DESCRIPTION OF THE EXEMPLARY EMBODIMENTS

Reducing the amount of air present in a stent-graft, stent, coil, or other prosthesis and their delivery systems may reduce the incidents of stroke and/or other damage that may result from air embolism. In accordance with an exemplary embodiment, systems and methods are provided that use perfluorochemicals (or "PFCs") to flush medical devices, such as stent-grafts, stents, coils, and/or their delivery systems, e.g., by absorbing the air during flushing. In addition, PFCs may be used to flush a medical device after flushing with other gasses (after using those gasses to flush out air) to remove those gasses. A perfluorocarbon liquid solution may, not just mechanically thrive out air (or other gas used to remove air) within the medical device, but may absorb air (or other gases) present in the medical device, thereby reducing the risk of an air embolism when the medical device is introduced and/or deployed within a patient's body. For example, degassed perfluorocarbon may have a relatively high solubility for air and other gases, such as carbon dioxide, such that may readily dissolve the air to remove it from exposure within the patient's body.

Any known pharmaceutical grade perfluorocarbons may be employed, such as perflubron, perfluorodecaline, perfluorotributylamine, perfluorohexane, perfluorononane, perfluoropentane, perfluorodichlorooctane, perfluoro-15-crown-5-ether, and the like. In an exemplary embodiment, the perfluorocarbons may also be employed in the form of an emulsion. One example is perfluorotributylamine emulsified with a non-ionic surfactant, which is a polymer of polyoxyethylene and polyoxypropylene, such as Pluronic F-68 or F-127.

Perfluorocarbons have been studied in the lungs and circulation and found to be bio-inert, minimally absorbed, and free of deleterious histological cellular or biochemical effects. The molecules are too large to be metabolized and can be eliminated in the lungs, urine and feces. They also have very high vapor pressures, and therefore evaporate quickly.

Perfluorochemicals (e.g., perfluorocarbons) have already been employed in "liquid breathing," which is a form of respiration in which a normally air-breathing organism breathes an oxygen-rich liquid (a perfluorocarbon) rather than breathing air. This procedure takes advantage of the fact that a common property of this class of chemicals is a high solubility for respiratory gases. In fact, these liquids carry more oxygen, carbon dioxide, and nitrogen than blood. The perfluorocarbons are used as oxygen-carriers intravenously infused to deliver oxygen to areas damaged by embolization and to use their solubility to increase the blood's ability to take up gases within the body.

Thus, in order to reduce the incidents of stroke by reducing the amount of air present in a stent-graft and its delivery system, the stent-graft and delivery system may be immersed in or flushed with the perfluorocarbon, preferably before being introduced into the body. It will be appreciated, however, that devices may also be flushed with perfluorocarbon even after introduction into a patient's body, e.g., to absorb any air present in the device during introduction. As opposed to the prior use of perfluorocarbons to deliver oxygen to areas damaged by embolization, or the use of flushing solutions to mechanically reduce the air by pushing it out of the stent-graft, the perfluorocarbons are employed to eliminate the air from the stent-grafts and their delivery-systems before it is introduced into the body. Optionally, the perfluorocarbons may then be removed from the stent-graft and delivery system prior to introduction into the body, e.g., by flushing with saline or other solutions typically used for flushing.

In addition or alternatively, degassed solutions and degassed PFC may be used for flushing of medical devices, such as stent-grafts, stents, coils, and their delivery systems, to remove air by absorbing the air during flushing. For example, solutions of perfluorocarbons, and other solutions, such as saline, may be degassed and thereby increase their ability to take up air during the flushing process. Degasification may be performed by applying vacuum to these solutions, boiling them, or by replacing an unwanted gas with another gas. After degasification of the flushing solution, the solution may be stored or otherwise maintained under atmospheric pressure, which maintains its degassed state by preventing solution of gases again.

In addition or alternatively, carbon dioxide may be used for high-pressure-flushing of medical devices, such as stent-grafts and their delivery systems, i.e., removing air by replacing the air with carbon dioxide. The carbon dioxide may afterwards be removed from the stent-grafts and their delivery system prior to introduction into the body, e.g., by flushing with PFC, saline or other solutions typically used for flushing. Carbon dioxide has a 22-fold higher solubility in blood compared to room air and therefore is preferred as a "trapped gas" when introduced and potentially released into the vasculature.

Turning to the drawings, FIG. 2 shows an exemplary embodiment of a stent-graft 10 carried by a delivery device 8 being flushed by a source of flushing solution 60. Generally, the delivery device 8 includes an introducer sheath, catheter, or other tubular member 20 including a proximal end 22, a distal end 24 sized for introduction into a patient's body, and one or more lumens extending therebetween, e.g., a lumen 26 within which the stent-graft 10 is loaded in a compressed or contracted condition at the distal end 24, as best seen in FIG. 2A. A handle or hub 50 may be provided on the proximal end 22 of the sheath 20 including a port 52 communicating with the lumen 26, e.g., including a valve 54 that may be selectively opened and closed.

Optionally, the delivery device 8 may include one or more additional components, e.g., a central cannula 30 also disposed within the lumen 26 and over which the stent-graft 10 may be loaded. The central cannula 30 may include an enlarged distal tip 34, e.g., to enclose a distal end of the lumen 26 and/or provide a rounded, tapered, or other atraumatic tip for the delivery device 8. The central cannula 30 may also include an instrument lumen (not shown) extending between proximal and distal ends thereof, e.g., sized to receive a guidewire or other rail, over which the delivery device 8 may be introduced into a patient's body. In addition or alternatively, the delivery device 8 may also include a pushed member 40 slidably received within the lumen 26 including a distal end 44 disposed adjacent the stent-graft 10.

For example, during use, the distal end 24 of the introducer sheath 20 (carrying the stent-graft 10) may be introduced into a patient's body, e.g., from a percutaneous entry site, and advanced to a target location, e.g., within the patient's aorta which is the site of an aneurysm (not shown). Once properly positioned, the sheath 20 may be retracted while maintaining the pusher member 30 substantially stationary to expose the stent-graft 10. The stent-graft 10 may be configured to resiliently expand within the target location automatically upon being exposed. Alternatively, the delivery device 8 may include a balloon or other expandable member (not shown), which may be inflated or otherwise manipulated to expand the stent-graft 10.

Prior to introduction of the delivery devices 8 into the patient's body, the source of flushing solution 60 may be used to flush the lumen 26 and/or stent-graft 10, e.g., to remove air. In an exemplary embodiment, the source 60 may contain a solution including one or more perfluorocarbons, as described elsewhere herein, which may be flushed into the lumen 26. For example, the solution may include an emulsion of perfluorocarbon and/or a degassed solution, as described elsewhere herein. In exemplary embodiments, the source 60 may be a syringe filled with the solution, a pump, or other container (not shown) that may be actuated to deliver the solution from the source 60 into the lumen 26 to flush the stent-graft 10.

With continued reference to FIG. 2, the valve 54 may be initially closed to prevent air from entering the port 52 and lumen 26. Tubing 62 may be coupled between the port 52 and the source 60, e.g., using luer lock or other connectors (not shown). Once the source 60 is coupled to the port 52, the valve 54 may be opened and the solution injected into the lumen 26 to flush the stent-graft 10. For example, the solution may pass through the port 52 and lumen 26 around and/or into the stent-graft 10 and exit the distal end 24 to remove any air bubbles trapped or otherwise located within folds of the stent-graft 10 and/or otherwise within the lumen 26. Once sufficiently flushed, the valve 54 may be closed and the source 60 disconnected from the port 52. The delivery device 8 may then be introduced into the patient's body, as described elsewhere herein.

Optionally, it may be desired to provide multiple sources of flushing fluids and/or sequences of flushes to enhance removal of air and/or any other trapped gases, e.g., using the source of perfluorocarbon 60 and one or more additional sources (not shown). For example, a source of gas may be provided that contains nitrogen or a bio-inert gas, e.g., argon or helium, which may be coupled to the port 52, similar to the source.

In an exemplary sequence, the source of gas may be coupled to the port 52 and used to flush the lumen 26 and stent-graft 10, thereby removing and/or displacing any air therein. Thus, if any gas remains within the lumen 26 and stent-graft 10, the air will be replaced by the carbon dioxide or bio-inert gas. Thereafter, the source of gas may be disconnected, and the source of perfluorocarbon 60 coupled to the port 52 and used to flush any remaining gas within the lumen 26 and stent-graft 10. The perfluorocarbon solution may easily dissolve the carbon dioxide or bio-inert gas, thereby more effectively flushing the device 8. Optionally, the source of perfluorocarbon 60 may be disconnected, and a source of saline, e.g., degassed saline, may then be coupled to the port 52 and used to further flush the lumen 26 and stent-graft 10.

It will be appreciated that the systems and methods herein may be used to flush and/or otherwise remove air from other devices before introduction into a patient's body. For example, a catheter, sheath, or other tubular device carrying a stent, coil, or other prosthesis or implant, may be flushed using any of the systems and methods described herein. In addition, it will be appreciated that the systems and methods herein may be used to flush and/or otherwise remove air from devices after introduction into a patient's body. Given the high solubility of air and other gases within perfluorocarbon liquid solutions, flushing with perfluorocarbon may more than mechanically thrive the air or gases from the device, but the chemical and/or physical properties of the fluorocarbon may dissolve and absorb the air or gases into the solution, thereby preventing their exposure or release within a patient's body.

In addition, it will be appreciated that stent-grafts, stents, or other prostheses may be exposed to perfluorocarbon solutions and/or sequences of gases and/or solutions, as described above, using other methods than flushing. For example, a prosthesis may be immersed in a perfluorocarbon solution, e.g., within a flushing and/or loading device, similar to those described in U.S. provisional application Ser. No. 62/247,287, filed Oct. 28, 2015, the entire disclosure of which is expressly incorporated by reference. In this method, the prosthesis may be inserted into the flushing device and one or more solutions and/or gases may be introduced into the device to remove air from the prosthesis. The prosthesis may then be loaded into a delivery device, which itself may also be flushed before and/or after loading the prosthesis.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

I claim:

1. A system for flushing air from a medical device, comprising:
   an elongate delivery device comprising a proximal end, a distal end, a lumen extending between the proximal and distal ends, and a port on the proximal end communicating with the lumen;
   a prosthesis carried by the delivery device within the lumen;
   a source of perfluorocarbon solution connectable to the port for flushing the lumen with the solution to remove air from one or both of the prosthesis and the lumen; and
   a source of gas comprising one of carbon dioxide and a bio-inert gas connectable to the port for flushing the lumen with the gas to remove air from one or both of the prosthesis and the lumen.

2. The system of claim 1, wherein the source of perfluorocarbon is connected to the port after flushing the lumen with the gas to remove the gas from one or both of the prosthesis and the lumen.

3. The system of claim 1, wherein the source of gas comprises one of argon and helium.

4. The system of claim 1, wherein the source of perfluorocarbon solution comprises degassed perfluorocarbon.

5. The system of claim 1, wherein the source of perfluorocarbon solution comprises an emulsion including perfluorocarbon.

6. The system of claim 1, wherein the prosthesis comprises one of a stent-graft, a stent, and a coil.

7. The system of claim 1, wherein the system further comprises instructions for use, wherein the instructions for use include instructions to expose the medical device to perfluorocarbon solution from the source of perfluorocarbon solution to remove gas from the medical device.

8. A system for flushing air from a medical device, comprising:
   an elongate delivery device comprising a proximal end, a distal end, a lumen extending between the proximal and distal ends, and a port on the proximal end communicating with the lumen;
   a prosthesis carried by the delivery device within the lumen;
   a source of perfluorocarbon solution connectable to the port for flushing the lumen with the solution to remove air from one or both of the prosthesis and the lumen; and
   a source of degassed saline connectable to the port for flushing the lumen with the degassed saline.

9. The system of claim 8, wherein the prosthesis comprises one of a stent-graft, a stent, and a coil.

10. The system of claim 8, wherein the source of perfluorocarbon solution comprises degassed perfluorocarbon.

11. The system of claim 8, wherein the source of perfluorocarbon solution comprises an emulsion including perfluorocarbon.

12. The system of claim 8, wherein the system further comprises instructions for use, wherein the instructions for use include instructions to expose the medical device to perfluorocarbon solution from the source of perfluorocarbon solution to remove gas from the medical device.

13. A method for removing gas from a medical device, comprising:
   providing a source of perfluorocarbon; and
   exposing the medical device to perfluorocarbon from the source of perfluorocarbon to remove air from the medical device.

14. The method of claim 13, wherein the medical device is exposed to the perfluorocarbon before the medical device is introduced into a patient's body.

15. The method of claim 13, further comprising introducing a distal end of the medical device into a patient's body.

16. The method of claim 13, wherein the source of perfluorocarbon contains degassed perfluorocarbon.

17. The method of claim 13, wherein the source of perfluorocarbon comprises an emulsion including perfluorocarbon.

18. The method of claim 13, wherein the medical device comprises a stent-graft constrained in a delivery condition.

19. The method of claim 18, wherein exposing the medical device comprises immersing the stent-graft in the source of perfluorocarbon to remove air trapped in the stent-graft.

20. The method of claim 18, wherein the stent-graft is carried by a catheter assembly in the delivery condition, and wherein exposing the medical device comprises:
   connecting one end of the catheter assembly to the source of perfluorocarbon; and
   flushing the perfluorocarbon through a lumen of the catheter assembly.

21. The method of claim 20, further comprising:
   removing the catheter assembly from the source of perfluorocarbon; and
   thereafter, flushing the lumen of the catheter assembly to remove perfluorocarbon from the stent-graft and catheter assembly.

22. A method for removing gas from a medical device, comprising:
   flushing the medical device with perfluorocarbon; and
   separately flushing the medical device with one or more of saline, carbon dioxide, and a bio-inert gas.

23. A method for preparing a medical device, comprising:
   flushing the medical device with a gas to displace air from the medical device; and
   thereafter, flushing the medical device with perfluorocarbon to dissolve and remove the gas.

24. The method of claim 23, further comprising flushing the medical device with saline after flushing the medical device with perfluorocarbon.

* * * * *